(12) United States Patent
Suzuki (10) Patent No.: US 9,262,667 B2
(45) Date of Patent: Feb. 16, 2016

(54) IMAGE ANALYSIS METHOD AND IMAGE ANALYSIS APPARATUS

(71) Applicant: OLYMPUS CORPORATION, Tokyo (JP)

(72) Inventor: Akemi Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/274,716

(22) Filed: May 10, 2014

(65) Prior Publication Data

US 2014/0247976 A1 Sep. 4, 2014

Related U.S. Application Data

(63) Continuation of application No. PCT/JP2012/075841, filed on Oct. 4, 2012.

(30) Foreign Application Priority Data

Nov. 10, 2011 (JP) .................................. 2011-246462

(51) Int. Cl.
*G06K 9/00* (2006.01)
*G06T 7/00* (2006.01)
*G02B 21/00* (2006.01)
*G02B 21/18* (2006.01)
*G01N 21/64* (2006.01)

(52) U.S. Cl.
CPC ........ *G06K 9/00147* (2013.01); *G02B 21/0076* (2013.01); *G02B 21/18* (2013.01); *G06K 9/0014* (2013.01); *G06T 7/0022* (2013.01); *G01N 21/6408* (2013.01); *G01N 21/6458* (2013.01)

(58) Field of Classification Search
CPC . G06K 9/00147; G06K 9/0014; G06T 7/0022
USPC .................................. 382/154, 100, 103, 218
See application file for complete search history.

(56) References Cited

U.S. PATENT DOCUMENTS

2008/0290293 A1 11/2008 Motomura
2009/0252414 A1 10/2009 Suzuki
(Continued)

FOREIGN PATENT DOCUMENTS

| JP | 2007-093277 | 4/2007 |
|---|---|---|
| JP | 2007-093371 | 4/2007 |
| JP | 2010237116 A * | 10/2010 |

(Continued)

OTHER PUBLICATIONS

Digman et al: "Detecting Protein Complexes in Living Cells from Laser Scanning Confocal Image Sequences by the Cross Correlation Raster Image Spectroscopy Method", BI, 2009.*

(Continued)

*Primary Examiner* — Ruiping Li
(74) *Attorney, Agent, or Firm* — Kenyon & Kenyon LLP (57) ABSTRACT

An image analysis method includes acquiring an image of at least one frame that comprises pixels, setting at least one analytic region for the image of at least one frame, extracting data on the pixel corresponding to each analytic region, setting time intervals for data pairs for use in correlation calculations, performing a correlation calculation for each of the time intervals by use of the extracted data, and performing a fitting for each of the correlation calculation results.

16 Claims, 9 Drawing Sheets

(56) References Cited

U.S. PATENT DOCUMENTS

2010/0225910 A1* 9/2010 Wagner-Conrad et al. ... 356/326
2012/0201463 A1 8/2012 Suzuki

FOREIGN PATENT DOCUMENTS

| JP | 2011-017677 | 1/2011 |
| WO | 2008/087869 | 7/2008 |
| WO | 2011/046211 | 4/2011 |
| WO | 2011/046212 | 4/2011 |

OTHER PUBLICATIONS

M. Digman et al., "Measuring Fast Dynamics in Solutions and Cells with a Laser Scanning Microscope," Biophysical Journal 89: 1317-1327 (2005).
International Search Report, dated Oct. 30, 2012, issued in corresponding International Application No. PCT/JP2012/075841.
European Supplementary Search Report, dated May 20, 2015, issued in corresponding European Patent Application No. 12848351.8.
Chinese Office Action, dated Aug. 5, 2015, issued in corresponding Chinese Patent Application No. 201280055334.8.

* cited by examiner

IMAGE ANALYSIS METHOD AND IMAGE ANALYSIS APPARATUS

CROSS-REFERENCE TO RELATED APPLICATIONS

This application is a Continuation application of PCT Application No. PCT/JP2012/075841, filed Oct. 4, 2012 and based upon and claiming the benefit of priority from prior Japanese Patent Applications No. 2011-246462, filed Nov. 10, 2011, the entire contents of which are incorporated herein by reference.

BACKGROUND

1. Field of the Invention

The present invention relates to an image analysis method and an image analysis apparatus.

2. Description of the Related Art

A technique for an image analysis called fluorescence cross-correlation spectroscopy (FCCS) has heretofore been known. The FCCS is shown in, for example, Jpn. Pat. Appln. KOKAI Publication No. 2007-093277. According to the FCCS, excitation light is continuously applied to one or more measurement points in a sample for a given length of time (e.g. for 10 seconds), and fluctuations of the intensity of fluorescence emitted from the measurement points are detected and correlatively analyzed to estimate the number of molecules and a diffusion constant.

A technique for an image analysis called a raster image correlation spectroscopy (RICS) has been also known. The RICS is shown in, for example, "Measuring Fast Dynamics in Solutions and Cells with a Laser Scanning Microscope", Michelle A. Digman, Claire M. Brown, Parijat Sengupta, Paul W. Wiseman, Alan R. Horwitz, and Enrico Gratton, Biophysical Journal, Vol. 89, P 1317-1327, August 2005. According to the RICS, one or more frames of raster scan images are acquired. The raster scan images may be, for example, fluorescence images. Data regarding each pixel of the fluorescence images represents information on the intensity of fluorescence generated from a point in a corresponding sample. The data regarding the pixels vary in the time and position of acquisition.

Correlation characteristics dependent on the fluctuations of molecules are obtained by a spatial autocorrelation analysis using the data regarding the pixels. A diffusion constant and the number of molecules can be found from the correlation characteristics of the molecules. A molecular diffusion time can be found from the diffusion constant.

Since the diffusion time and the number of molecules can be thus evaluated by the spatial autocorrelation analysis, an interaction between the molecules can be observed.

SUMMARY

An image analysis method according to the present invention comprises acquiring an image of at least one frame that comprises pixels, setting at least one analytic region for the image of at least one frame, extracting data on the pixel corresponding to each analytic region, setting time intervals for data pairs for use in correlation calculations, performing a correlation calculation for each of the time intervals by use of the extracted data, and performing a fitting for each of the correlation calculation results.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute apart of the specification, illustrate embodiments of the invention, and together with the general description given above and the detailed description of the embodiments given below, serve to explain the principles of the invention.

DESCRIPTION OF EMBODIMENT

An embodiment of the present invention will now be described with reference to the drawings.

[Apparatus Configuration]

Figure 1:
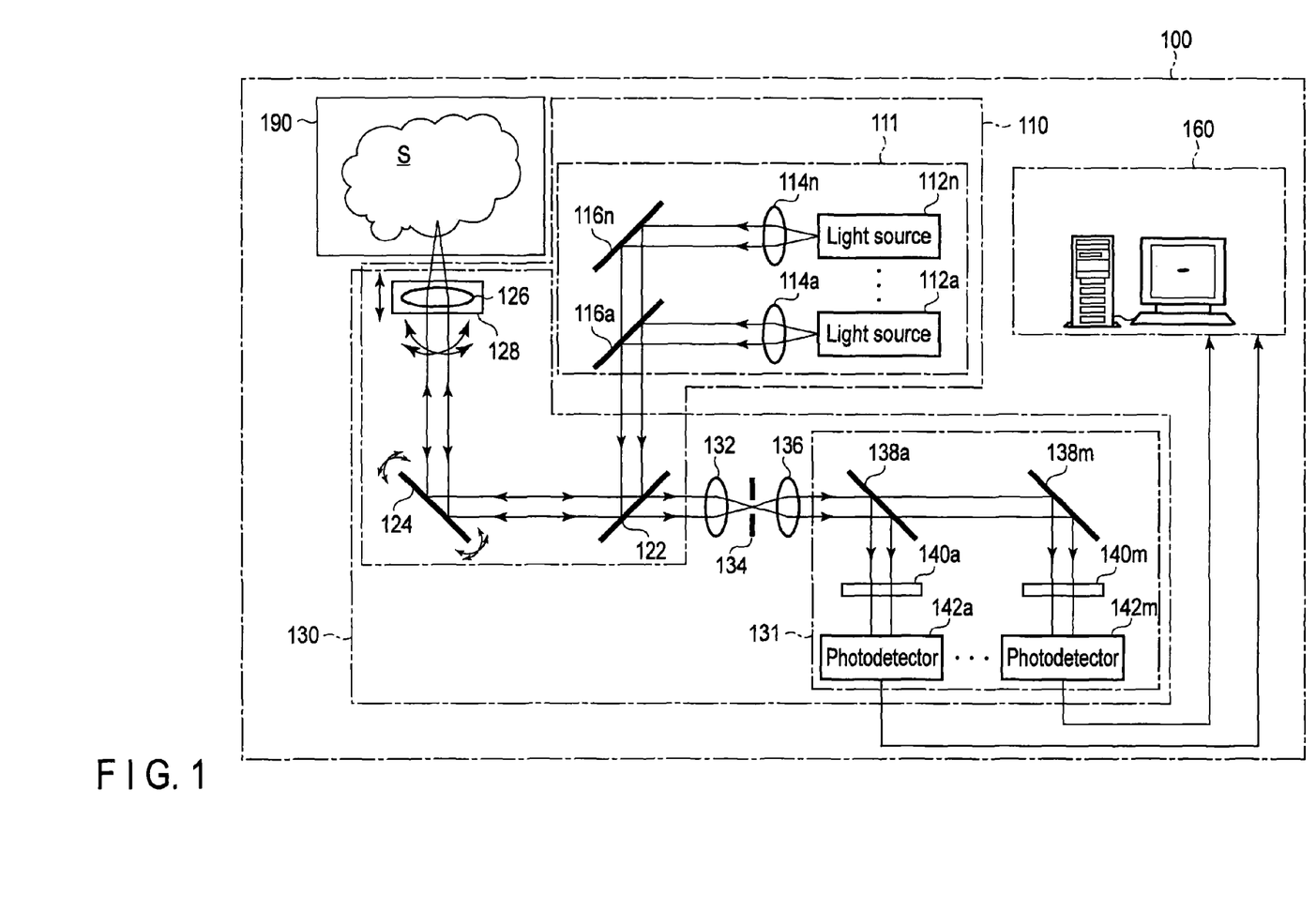
FIG. 1 schematically shows an image analysis apparatus according to one embodiment.

FIG. 1 schematically shows an image analysis apparatus according to one embodiment. This image analysis apparatus has a configuration based on a scanning confocal optical microscope for a fluorescence observation of a sample.

As shown in FIG. 1, an image analysis apparatus 100 has a light application section 110 to apply light such as excitation light to a sample S, a light detection section 130 to detect light such as fluorescence from the sample S, a control section 160 to perform control necessary for an image analysis, and a sample stage 190, which supports the sample S.

The sample S is contained in a sample container such as a microplate or a slide glass, and mounted on the sample stage 190. The sample stage 190 supports, for example, the sample S movably in a lateral direction (xy-direction) and in a height direction (z-direction) relative to the light application section 110 and the light detection section 130. For example, the sample stage 190 includes three stepping motors having their output shafts that intersect at right angles with one another. The sample S can be moved in the xyz-direction by these stepping motors.

The image analysis apparatus 100 is, for example, a multiple light irradiation-multiple light detection type. Thus, the light application section 110 includes an n-channel light source section 111, and the light detection section 130 includes an m-channel light detection section 131. The light source section 111 has n channels, and can radiate excitation light beams of n kinds of different wavelengths. The light detection section 131 has m channels, and can detect fluorescence of m kinds of different wavelengths. The light source section 111 does not always need to have more than one channel, and may only have one channel. The light detection section 131 does not always need to have more than one channel, and may only have one channel.

The n-channel light source section 111 of the light application section 110 includes light sources 112a, ..., 112n, collimating lenses 114a, ..., 114n, and dichroic mirrors 116a, ..., 116n. The light sources 112a, ..., 112n emit excitation light to excite fluorescent dyes included in the sample S to the sample S to emit light (fluorescence). The wavelengths of the excitation light emitted from the light sources 112a, ..., 112n are different from one another to correspond to the kinds of fluorescent dyes included in the sample S. The light sources 112a, ..., 112n comprise, for example, laser light sources of oscillation wavelengths corresponding to the fluorescent dyes in the sample S. The collimating lenses 114a, ..., 114n collimate the excitation light emitted from the light sources 112a, ..., 112n, respectively. The dichroic mirrors 116a, ..., 116n reflect, in the same direction, the excitation light that has passed through the collimating lenses 114a, ..., 114n, respectively. The dichroic mirrors 116a, ..., 116n respectively transmit the excitation light entering from the upper side in FIG. 1, and reflect the excitation light entering from the right side in FIG. 1. As a result, the excitation light of different wavelengths respectively emitted from the light sources 112a, ..., 112n are combined into a beam after passing through the dichroic mirror 116a. The dichroic mirror 116n does not need to transmit the excitation light, and may therefore be changed to a simple mirror.

The light application section 110 further includes a dichroic mirror 122, a galvano-mirror 124, an objective lens 126, and an objective lens drive mechanism 128. The dichroic mirror 122 reflects the excitation light from the light source section 111 to the galvano-mirror 124, and transmits the fluorescence emitted from the sample S. The galvano-mirror 124 reflects the excitation light to the objective lens 126, and changes its reflection direction. The objective lens 126 converges the excitation light and then applies the excitation light to a measurement point in the sample S, and takes in the light from the measurement point in the sample S. The objective lens used as the objective lens 126 has a high numerical aperture (NA) to form a micro confocal region (measurement point). The confocal region to be thereby obtained has a substantially cylindrical shape that is sized at approximately 0.6 μm in diameter (in an xy-plane) and approximately 2 μm length (in the z-direction). The galvano-mirror 124 constitutes an xy-scan mechanism to scan the measurement point in the xy-direction. The xy-scan mechanism may be constituted by using a acoustooptical modulator (AOM), a polygon mirror, or a hologram scanner instead of the galvano-mirror. The objective lens drive mechanism 128 moves the objective lens 126 along the optical axis. As a result, the measurement point is moved in the z-direction. That is, the objective lens drive mechanism 128 constitutes a z-scan mechanism to scan the measurement point in the z-direction.

The light detection section 130 and the light application section 110 commonly include the objective lens 126, the galvano-mirror 124, and the dichroic mirror 122. The light detection section 130 further includes a converging lens 132, a pin hole 134, and a collimating lens 136. The converging lens 132 converges the light that has passed through the dichroic mirror 122. The pin hole 134 is located in the focus of the converging lens 132. That is, the pin hole 134 is located at a position that is conjugate to the measurement point in the sample S, and selectively allows only the light from the measurement point to pass therethrough. The collimating lens 136 collimates the light that has passed through the pin hole 134. The light that has passed through the collimating lens 136 enters the m-channel light detection section 131.

The m-channel light detection section 131 includes dichroic mirrors 138a, ..., 138m, fluorescence filters 140a, ..., 140m, photodetectors 142a, ..., 142m. The dichroic mirrors 138a, ..., 138m selectively reflect light of wavelengths located in the vicinity of the wave range of the fluorescence to be detected, respectively. The dichroic mirror 138m does not need to transmit the light, and may therefore be changed to a simple mirror. The fluorescence filters 140a, ..., 140m respectively cut off the light of undesired wavelength components out of the light reflected by the dichroic mirrors 138a, ..., 138m, and selectively transmit the fluorescence generated by the excitation light from the light sources 112a, ..., 112n. The fluorescence that has passed through the fluorescence filters 140a, ..., 140m enter the photodetectors 142a, ..., 142m, respectively. The photodetectors 142a, ..., 142m output signals corresponding to the intensities of the light that has entered. That is, the photodetectors 142a, ..., 142m output fluorescence intensity signals from the measurement point in the sample S.

The control section 160 comprises, for example, a personal computer. The control section 160 performs the acquisition, storage, and display of fluorescence images of observation regions of the sample S, waiting for an input such as a setting of an analytic region, and analytic processing of images (e.g. calculation of a correlation value, and estimation of the number of molecules and a diffusion time). The control section 160 also controls the galvano-mirror 124, which is the xy-scan mechanism, the objective lens drive mechanism 128, which is the z-scan mechanism, and the sample stage 190.

Figure 2:
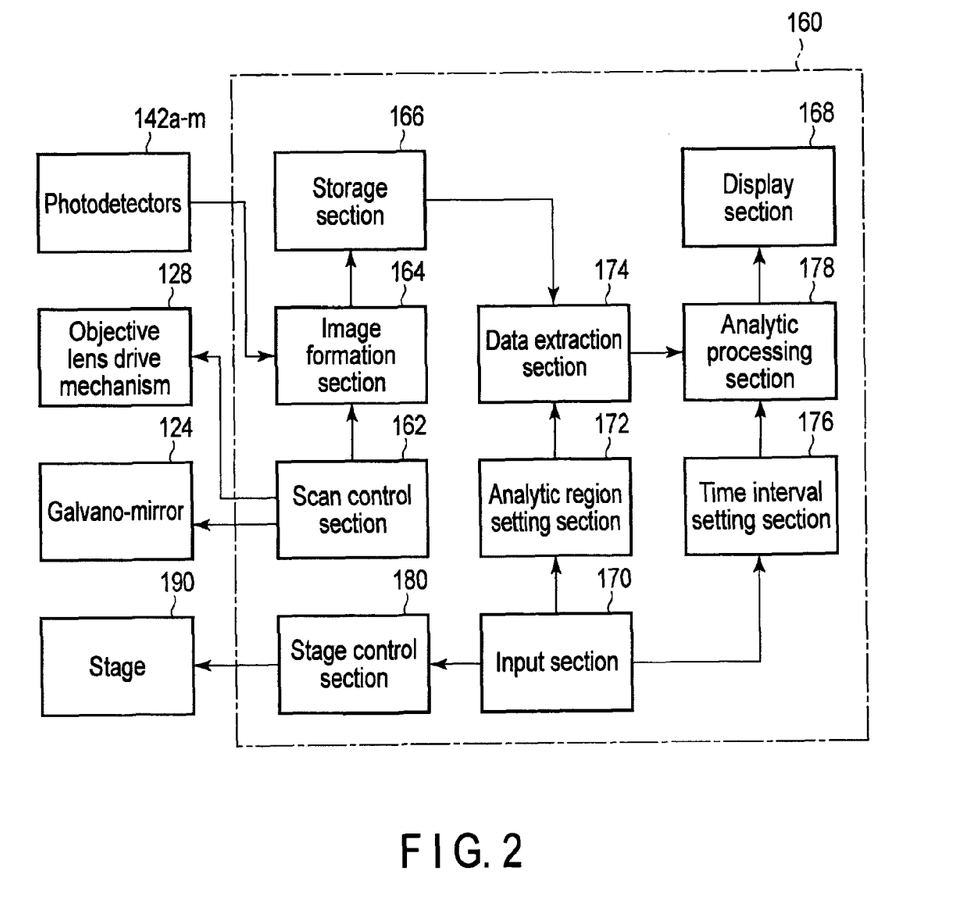
FIG. 2 shows functional blocks of a control section shown in FIG. 1.

Functional blocks of the control section shown in FIG. 1 are shown in FIG. 2. As shown in FIG. 2, the control section 160 includes a scan control section 162, an image formation section 164, a storage section 166, a display section 168, an input section 170, an analytic region setting section 172, a data extraction section 174, an analytic processing section 178, a time interval setting section 178, and a stage control section 180. The scan control section 162, the image formation section 164, the storage section 166, and the stage control section 180 cooperate with the light application section 110 and the light detection section 130 described above to constitute an image acquisition section.

The scan control section 162 controls the galvano-mirror 124 to raster-scan an application position of the excitation light in the sample S when a fluorescence image of the sample S is acquired. If necessary, the scan control section 162 also controls the objective lens drive mechanism 128 to z-scan the application position of the excitation light in the sample S. The image formation section 164 forms a fluorescence image of the sample S from information on the application position of the excitation light input from the scan control section 162 and output signals of the photodetectors 142a, ..., 142m. As a result, the fluorescence image is acquired. The fluorescence image formed by the image formation section 164 is stored in the storage section 166. The display section 168 displays the fluorescence image of the sample S and an analytic processing result. The input section 170 includes, for example, a mouse and a keyboard, and cooperates with the display section 168 to constitute a GUI. This GUI is used to set an observation region and an analytic region. The stage control section 180 controls the sample stage 190 in accordance with input information from the input section 170 to set, for example, an observation region. The analytic region setting section 172 sets an analytic region in accordance with input information from the input section 170. The data extraction section 174 extracts data on the analytic region for which correlation calculations are to be performed. The time interval setting section 176 sets time intervals of pairs of data used in the correlation calculations. The analytic processing section 178 performs the correlation calculations by using data on the pixels of the image of the analytic region. The processing in the analytic processing section 178 will be described in detail later.

As shown in FIG. 1, the excitation light emitted from the light sources 112a, . . . , 112n is applied to the measurement point in the sample S through the collimating lenses 114a, 114n, the dichroic mirrors 116a, . . . , 116n, the dichroic mirror 122, the galvano-mirror 124, and the objective lens 126. The measurement point to which the excitation light is applied is raster-scanned with the galvano-mirror 124 in the xy-direction. If necessary, the measurement point is z-scanned with the objective lens drive mechanism 128 whenever one raster-scan ends. The measurement point is scanned over the whole observation region. The sample S that has received the excitation light generates fluorescence from the measurement point. The light (including undesired reflected light in addition to the fluorescence) from the sample S reaches the pin hole 134 through the objective lens 126, the galvano-mirror 124, the dichroic mirror 122, and the converging lens 132. Since the pin hole 134 is located at the position that is conjugate to the measurement point, the light from the measurement point in the sample S only passes through the pin hole 134. The light that has passed through the pin hole 134, that is, the light from the measurement point in the sample S enters the m-channel light detection section 131 through the collimating lens 136. The light that has entered the m-channel light detection section 131 is split (i.e. dispersed) in accordance with the wavelengths by the dichroic mirrors 138a, . . . , 138m, and undesired components are removed by the fluorescence filters 140a, . . . , 140m. The fluorescence that has passed through the fluorescence filters 140a, . . . , 140m enters the photodetectors 142a, . . . , 142m, respectively. The photodetectors 142a, . . . , 142m respectively output fluorescence intensity signals indicating the intensities of the incident light, that is, the fluorescence emitted from the measurement point in the sample S. The fluorescence intensity signals are input to the image formation section 164. The image formation section 164 processes the input fluorescence intensity signals synchronously with positional information in the xy-direction (and the z-direction) to form a fluorescence image of the observation region in the sample S. The formed fluorescence image is saved in the storage section 166. The fluorescence image saved in the storage section 166 is displayed on the display section 168 as it is, or processed by the analytic processing section 178, and an analytic processing result is displayed on the display section 168.

[Analytic Procedure]

Figure 3:
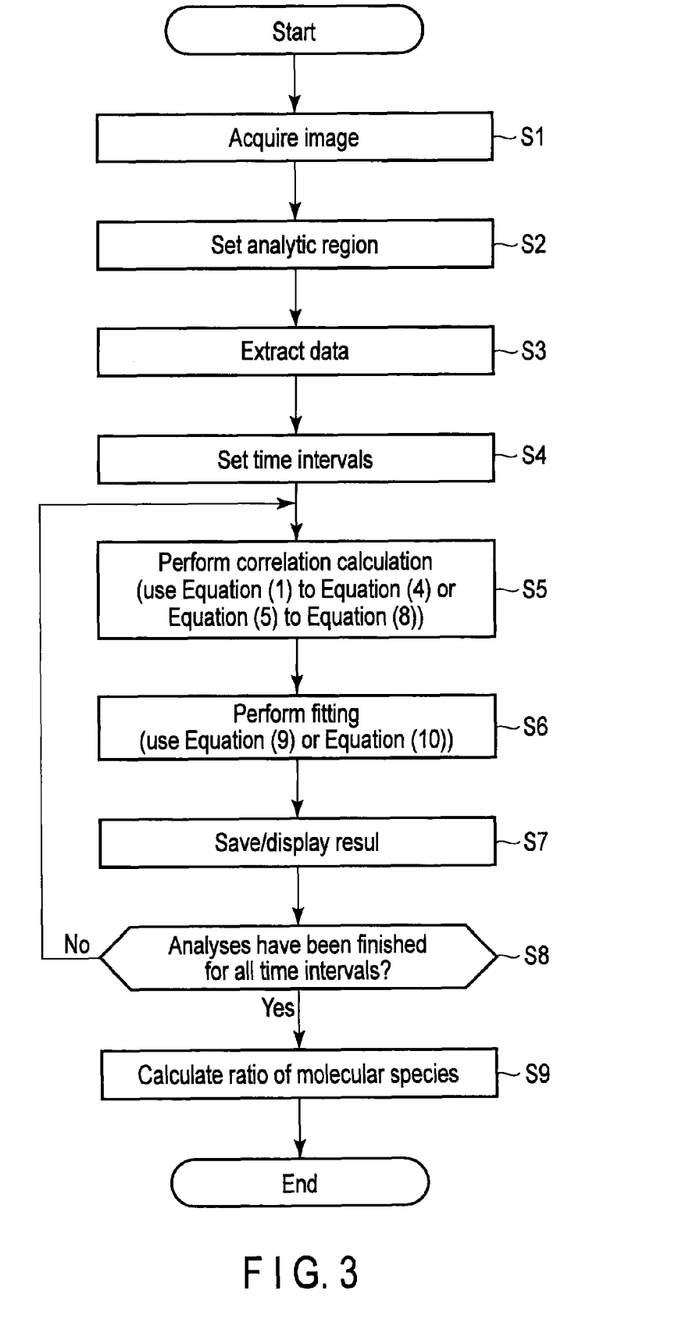
FIG. 3 is a flowchart of an image analysis according to one embodiment.

A procedure of an image analysis is described below with reference to FIG. 3. Steps are described by proper reference to FIG. 4 to FIG. 11.

(Step S1)

An image or images, for example a fluorescence image or fluorescence images, of a frame or frames of the observation region of the sample S is acquired. The fluorescence image is acquired through one channel of the light source section 111, and one channel of the light detection section 131 corresponding thereto. The fluorescence image of each frame comprises pixels the data of which have been acquired in a time-series manner by the scan of the excitation light. The measurement point actually has spatial expansions in the xyz-direction, and the pixel has a size corresponding to the spatial expansions of the measurement point. The data on each pixel of the fluorescence image is, for example, the intensity of the fluorescence emitted from the corresponding measurement point.

The observation region is a two-dimensional region or a three-dimensional region, and the fluorescence image is a two-dimensional image or a three-dimensional image accordingly. When the observation region is the two-dimensional region, the fluorescence image is the two-dimensional image in which pixels having sizes in the xy-direction are two-dimensionally arranged. When the observation region is the three-dimensional region, the fluorescence image is the three-dimensional image in which pixels having sizes in the xyz-direction are three-dimensionally arranged. From a different point of view, the three-dimensional image comprises two-dimensional images of frames having different z-positions.

Figure 4:
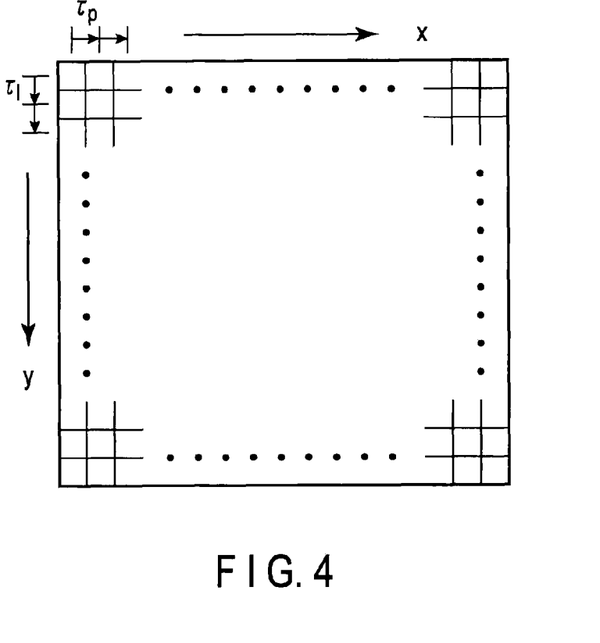
FIG. 4 shows a fluorescence image of a two-dimensional image of one frame.

A fluorescence image of a two-dimensional image of one frame is shown in FIG. 4. In FIG. 4, $\tau_p$ is the difference (pixel time) of acquisition time between a certain pixel and a next pixel adjacent thereto. That is, the pixel time $\tau_p$ is a time required to acquire data for one pixel. $\tau_l$ is the difference (line time) of acquisition time between an initial pixel of a certain line and an initial pixel of a next line. That is, the line time $\tau_l$ means a time required to scan one line.

Figure 5:
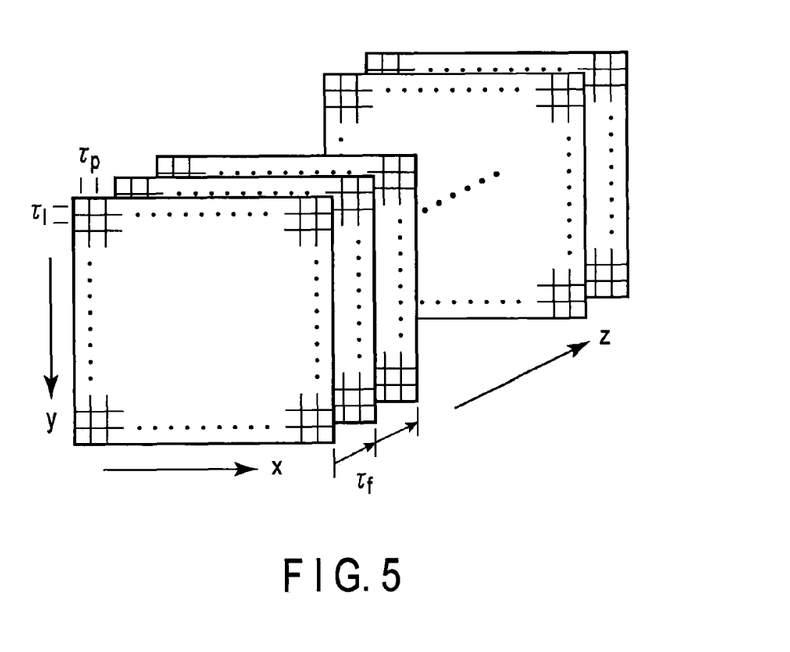
FIG. 5 shows fluorescence images of a three-dimensional image of one frame.

A three-dimensional image of one frame is shown in FIG. 5. In FIG. 5, $\tau_p$ is a pixel time, $\tau_l$ is a line time, and $\tau_f$ is the difference (frame time) of acquisition time between an initial pixel of a certain frame and an initial pixel of a next frame. That is, the frame time $\tau_f$ means a time required to scan one frame.

(Step S2)

Figure 6:
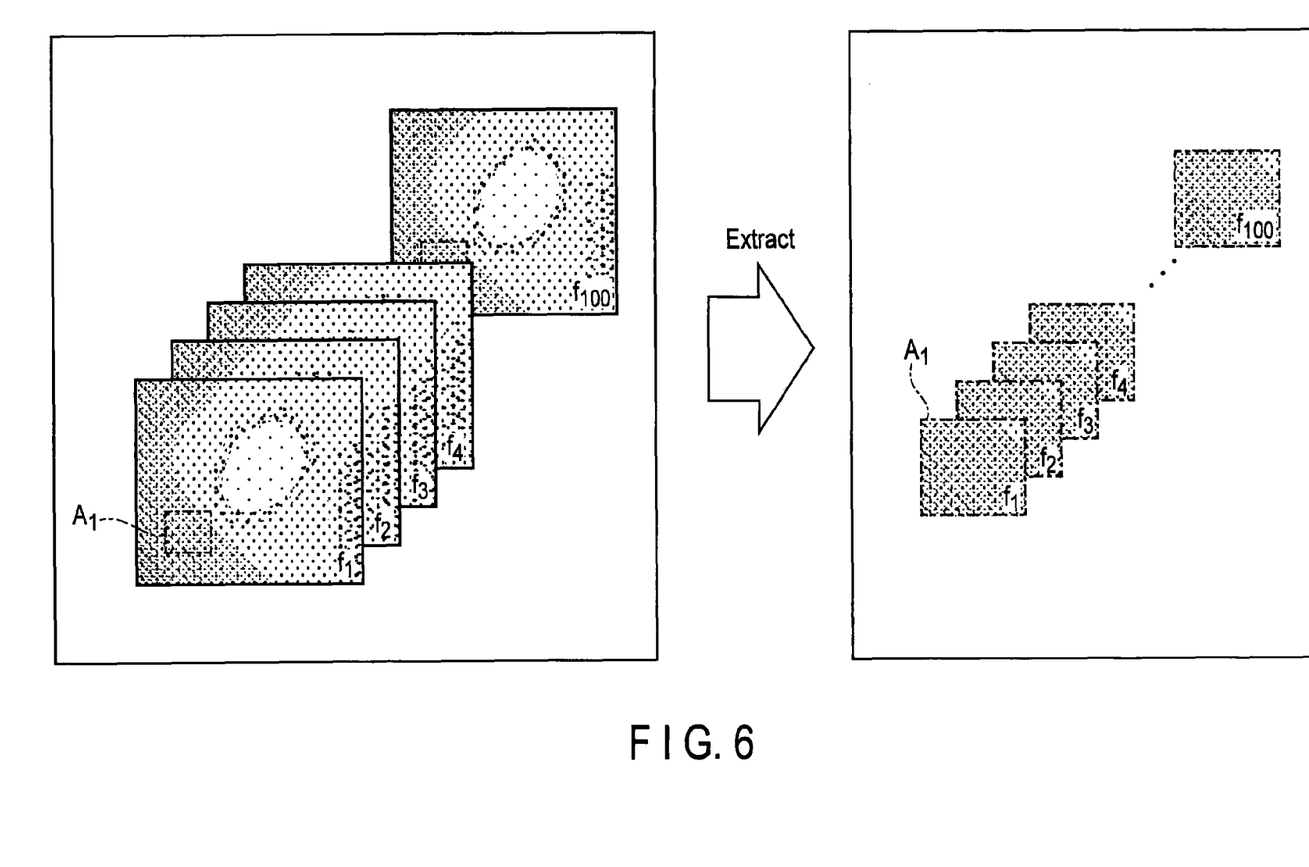
FIG. 6 shows images of observation regions of frames and an extracted image of one analytic region.
Figure 7:
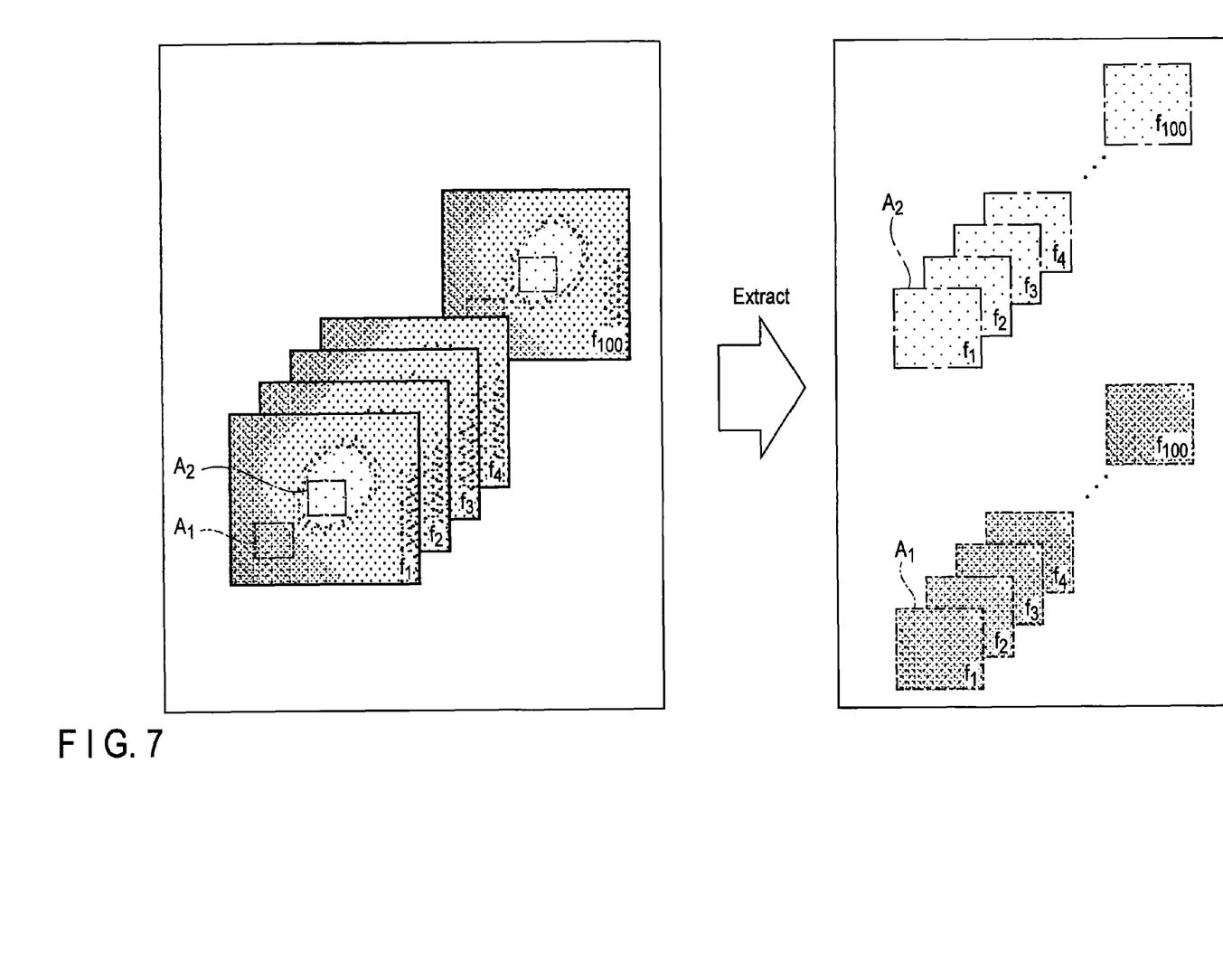
FIG. 7 shows images of observation regions of frames and extracted images of two analytic regions.

One or more analytic regions are set for the image, for example, the fluorescence image of the observation region of one frame or each of frames that has been acquired. The analytic regions are spatially different regions, and are normally separate from one another and do not overlap. The analytic region is a two-dimensional region for a two-dimensional observation region, and is normally a three-dimensional region but may be a two-dimensional region for a three-dimensional observation region. In FIG. 6, when 100 frames are acquired, one analytic region $A_1$ is set for a fluorescence image of the observation region of each of frames $f_1$ to $f_{100}$), and the analytic region $A_1$ is located outside a nucleus of a cell. In FIG. 7, two analytic regions $A_1$ and $A_2$ are set for a fluorescence image of the observation region of each of frames $f_1$ to $f_{100}$), and the analytic region $A_1$ is located outside a nucleus of a cell, while the analytic region $A_2$ is located inside the nucleus of the cell.

(Step S3)

Data on the pixel corresponding to each analytic region is extracted. In FIG. 6, the extracted data, that is, images of the pixels of the analytic region $A_1$ of the frames $f_1$ to $f_{100}$ are shown. In FIG. 7, the extracted data, that is, images of the pixels of the analytic regions $A_1$ and $A_2$ of the frames $f_1$ to $f_{100}$) are shown.

(Step S4)

Time intervals (delay times) of data pairs for use in correlation calculations are set. Each time interval corresponds to the different of acquisition time of the data on pixels of the pairs used in a product-sum calculation for each correlation calculation. For example, one time interval corresponds to two pixels in the same analytic region or different analytic regions of the same frame, and another time interval corresponds to two pixels in the same analytic region or different analytic regions of different frames. These time intervals are preferably set so that a sufficient number of product-sum calculations can be performed.

(Step S5)

The extracted data on the pixels are used to perform the correlation calculations. The calculation formula used in the correlation calculations varies by whether the image of the analytic region is the two-dimensional image or the three-dimensional image. Moreover, the calculation formula varies by whether two pixels of each of data pairs for use in the product-sum calculations of the correlation calculation belong to the same analytic region or different analytic regions. In addition, the calculation formula varies by whether two pixels of each of data pairs for use in the product-sum calculations of the correlation calculation belong to the image of the same frame or the images of different frames.

The calculation formulas to be applied to the two-dimensional image are as follows.

Figure 8:
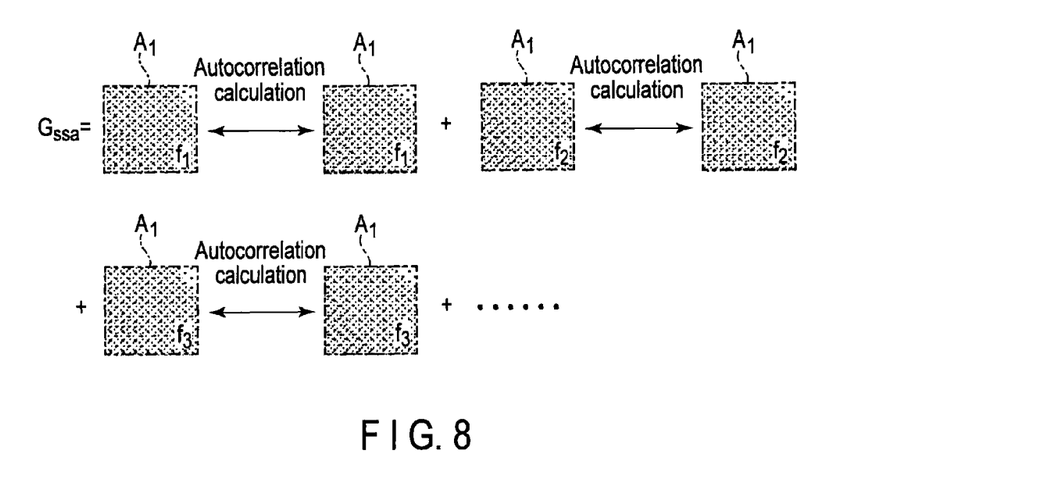
FIG. 8 schematically shows a correlation calculation for the same analytic region in the image of the same frame.

1. Two pixels of each data pair belong to the image of the same analytic region, and belong to the image of the same frame. In this case, pairs of data on the pixels in the same analytic region in the image of the same frame are used to perform a correlation calculation. This correlation calculation is an autocorrelation calculation. FIG. 8 schematically shows the correlation calculation in this case.

$$G_{2ssa}(\xi, \psi) = \frac{\sum I_{f_i}(x, y) * I_{f_i}(x+\xi, y+\psi)/M_{ii}}{(\sum I_{f_i}(x, y)/M_i)^2} \quad (1)$$

where $G_{2ssa}$ is an autocorrelation value in the same analytic region $A_1$ of the same frame $f_i$, $I_{fi}$ is data, for example, fluorescence intensity data on the pixels of the image of the analytic region $A_1$ of the frame $f_i$, x, y are spatial coordinates of a measurement point, $\xi$, $\psi$ are variations of the spatial coordinates from the measurement point, $M_{ii}$ is the number of product-sum calculations of the data on the pixels of the image of the analytic region $A_1$ of the frame $f_i$, and $M_i$ is the total number of data on the pixels of the image of the analytic region $A_1$ of the frame $f_i$.

Figure 9:
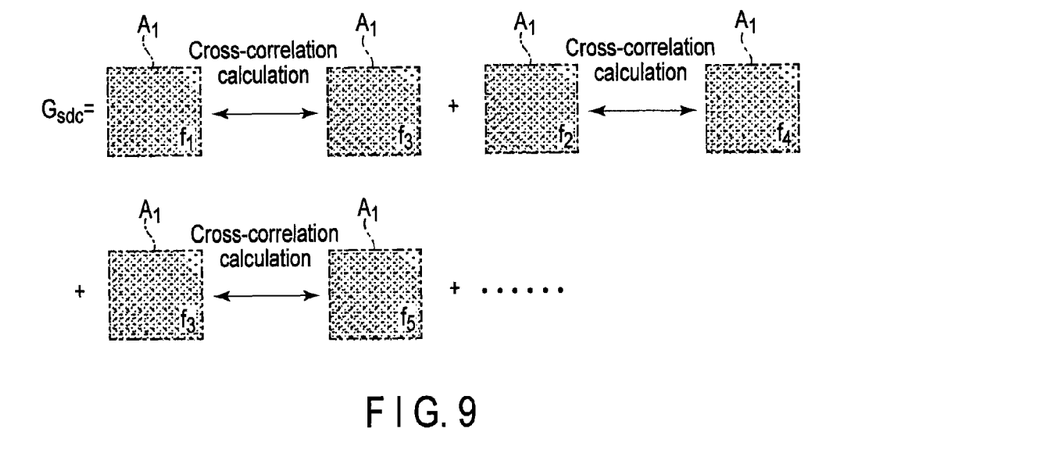
FIG. 9 schematically shows a correlation calculation for the same analytic region in the images of different frames.

2. Two pixels of each data pair belong to the image of the same analytic region, and belong to the images of different frames. In this case, pairs of data on the pixels in the same analytic region in the image of the same frame are used to perform a correlation calculation. This correlation calculation is a cross-correlation calculation. FIG. 9 schematically shows the correlation calculation in this case.

$$G_{2sdc}(\xi, \psi) = \frac{\sum I_{f_i}(x, y) * I_{f_j}(x+\xi, y+\psi)/M_{ij}}{(\sum I_{f_i}(x, y)/M_i)(\sum I_{f_j}(x, y)/M_j)} \quad (2)$$

where $G_{2sdc}$ is a cross-correlation value in the same analytic region $A_1$ of a frame $f_i$ and a frame $f_j$ that are different from each other, $I_{fi}$ is data, for example, fluorescence intensity data on the pixels of the image of the analytic region $A_1$ of the frame $f_i$, $I_{fj}$ is data, for example, fluorescence intensity data on the pixels of the image of the analytic region $A_1$ of the frame $f_j$, x, y are spatial coordinates of a measurement point, $\xi$, $\psi$ are variations of the spatial coordinates from the measurement point, $M_{ij}$ is the number of product-sum calculations of the data on the pixels of the image of the same analytic region $A_1$ of the frame $f_i$ and frame $f_j$, $M_i$ is the total number of data on the pixels of the image of the analytic region $A_1$ of the frame $f_i$, and $M_j$ is the total number of data on the pixels of the image of the analytic region $A_1$ of the frame $f_j$.

Figure 10:
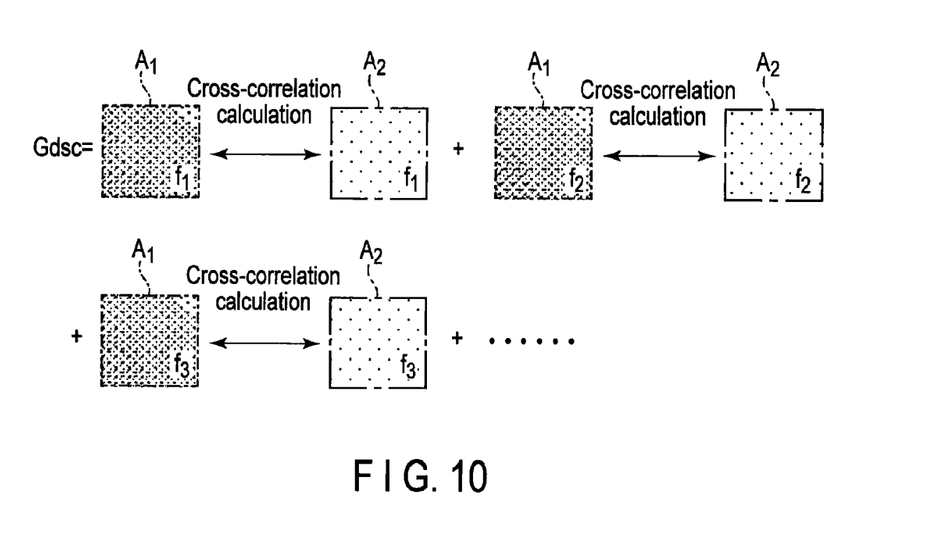
FIG. 10 schematically shows a correlation calculation for different analytic regions in the image of the same frame.

3. Two pixels of each data pair belong to the images of different analytic regions, and belong to the image of the same frame. In this case, pairs of data on the pixels in different analytic regions in the images of different frames are used to perform a correlation calculation. This correlation calculation is a cross-correlation calculation. FIG. 10 schematically shows the correlation calculation in this case.

$$G_{2dsc}(\xi, \psi) = \frac{\sum I_{1f_i}(x, y) * I_{2f_i}(x+\xi, y+\psi)/M_{12ii}}{(\sum I_{1f_i}(x, y)/M_{1i})(\sum I_{2f_i}(x, y)/M_{2i})} \quad (3)$$

where $G_{2dsc}$ is a cross-correlation value between different analytic regions $A_1$ and $A_2$ of the same frame $f_i$, $I_{1fi}$ is data, for example, fluorescence intensity data on the pixels of the image of the analytic region $A_1$ of the frame $f_i$, $I_{2fi}$ is data, for example, fluorescence intensity data on the pixels of the image of the analytic region $A_2$ of the frame $f_i$, x, y are spatial coordinates of a measurement point, $\xi$, $\psi$ are variations of the spatial coordinates from the measurement point, $M_{12ii}$ is the number of product-sum calculations of the data on the pixels of the images of the different analytic regions $A_1$ and $A_2$ of the frame $f_i$, $M_{1i}$ is the total number of data on the pixels of the image of the analytic region $A_1$ of the frame $f_i$, and $M_{2i}$ is the total number of data on the pixels of the image of the analytic region $A_2$ of the frame $f_i$.

Figure 11:
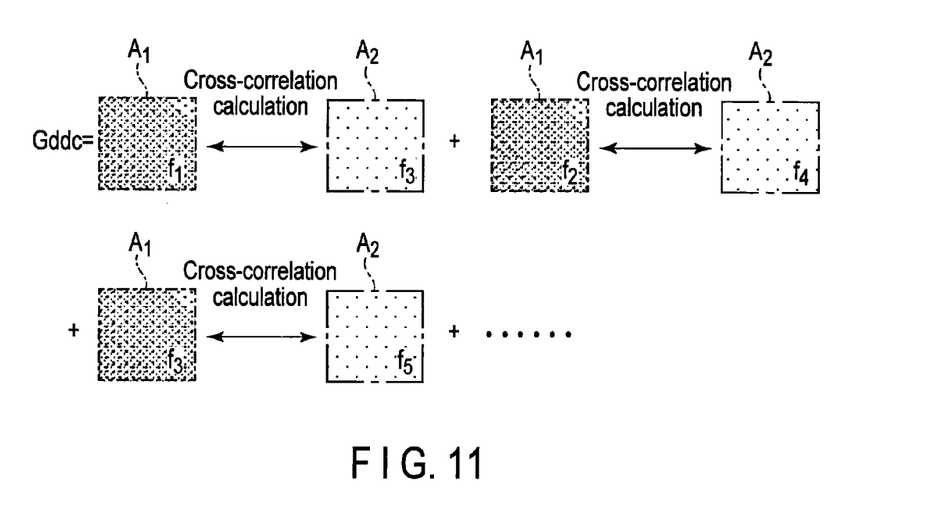
FIG. 11 schematically shows a correlation calculation for different analytic regions in the images of different frames.

4. Two pixels of each data pair belong to the images of different analytic regions, and belong to the image of the different frame. In this case, pairs of data on the pixels in different analytic regions in the images of different frames are used to perform a correlation calculation. This correlation calculation is a cross-correlation calculation. FIG. 11 schematically shows the correlation calculation in this case.

$$G_{2ddc}(\xi, \psi) = \frac{\sum I_{1f_i}(x, y) * I_{2f_j}(x+\xi, y+\psi)/M_{12ij}}{(\sum I_{1f_i}(x, y)/M_{1i})(\sum I_{2f_j}(x, y)/M_{2j})} \quad (4)$$

where $G_{2ddc}$ is a cross-correlation value between the analytic region $A_1$ of the frame $f_i$ and the analytic region $A_2$ of the same $f_j$, $I_{1fi}$ is data, for example, fluorescence intensity data on the pixels of the image of the analytic region $A_1$ of the frame $f_i$, $I_{2fj}$ is data, for example, fluorescence intensity data on the pixels of the image of the analytic region $A_2$ of the frame $f_j$, x, y are spatial coordinates of a measurement point, $\xi$, $\psi$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$ is the total number of data on the pixels of the image of the analytic region $A_1$ of the frame $f_i$, and $M_{2j}$ is the total number of data on the pixels of the image of the analytic region $A_2$ of the frame $f_j$.

The calculation formulas to be applied to the three-dimensional image are as follows.

1. Two pixels of each data pair belong to the image of the same analytic region, and belong to the image of the same frame. In this case, pairs of data on the pixels in the same analytic region in the image of the same frame are used to perform a correlation calculation. This correlation calculation is an autocorrelation calculation.

$$G_{3ssa}(\xi, \psi, \eta) = \frac{\sum I_{f_i}(x, y, z) * I_{f_i}(x+\xi, y+\psi, z+\eta)/M_{ii}}{(\sum I_{f_i}(x, y, z)/M_i)^2} \quad (5)$$

where $G_{3ssa}$ is an autocorrelation value of the same analytic region $A_1$ of the same frame $f_i$, $I_{fi}$ is data, for example, fluorescence intensity data on the pixels of the image of the analytic region $A_1$ of the frame $f_i$, x, y, z are spatial coordinates of a measurement point, $\xi$, $\psi$, $\eta$ are variations of the spatial coordinates from the measurement point, $M_{ii}$ is the number of product-sum calculations of the data on the pixels of the image of the analytic region $A_1$ of the frame $f_i$, and $M_i$ is the total number of data on the pixels of the image of the analytic region $A_1$ of the frame $f_i$.

2. Two pixels of each data pair belong to the image of the same analytic region, and belong to the images of different frames. In this case, pairs of data on the pixels in the same analytic region in the images of different frames are used to perform a correlation calculation. This correlation calculation is a cross-correlation calculation.

$$G_{3sdc}(\xi, \psi, \eta) = \frac{\sum I_{f_i}(x, y, z) * I_{f_j}(x+\xi, y+\psi, z+\eta)/M_{ij}}{(\sum I_{f_i}(x, y, z)/M_i)(\sum I_{f_j}(x, y, z)/M_{ij})} \quad (6)$$

where $G_{3sdc}$ is a cross-correlation value in the same analytic region $A_1$ of a frame $f_i$ and a frame $f_j$ that are different from each other, $I_{fi}$ is data, for example, fluorescence intensity data on the pixels of the image of the analytic region $A_1$ of the frame $f_i$, $I_{fj}$ is data, for example, fluorescence intensity data on the pixels of the image of the analytic region $A_1$ of the frame $f_j$, x, y, z are spatial coordinates of a measurement point, $\xi$, $\psi$, $\eta$ are variations of the spatial coordinates from the measurement point, $M_{ij}$ is the number of product-sum calculations of the data on the pixels of the image of the same analytic region $A_1$ of the frame $f_i$ and frame $f_j$, $M_i$ is the total number of data on the pixels of the image of the analytic region $A_1$ of the frame $f_i$, and $M_j$ is the total number of data on the pixels of the image of the analytic region $A_1$ of the frame $f_j$.

3. Two pixels of each data pair belong to the images of different analytic regions, and belong to the image of the same frame. In this case, pairs of data on the pixels in different analytic regions in the image of the same frame are used to perform a correlation calculation. This correlation calculation is a cross-correlation calculation.

$$G_{3dsc}(\xi, \psi, \eta) = \frac{\sum I_{1f_i}(x, y, z) * I_{2f_i}(x+\xi, y+\psi, z+\eta)/M_{12ii}}{(\sum I_{1f_i}(x, y, z)/M_{1i})(\sum I_{2f_i}(x, y, z)/M_{2i})} \quad (7)$$

where $G_{3dsc}$ is a cross-correlation value between different analytic regions $A_1$ and $A_2$ of the same frame $f_i$, $I_{1fi}$ is data, for example, fluorescence intensity data on the pixels of the image of the analytic region $A_1$ of the frame $f_i$, $I_{2fi}$ is data, for example, fluorescence intensity data on the pixels of the image of the analytic region $A_2$ of the frame $f_i$, x, y, z are spatial coordinates of a measurement point, $\xi$, $\psi$, $\eta$ are variations of the spatial coordinates from the measurement point, $M_{12ii}$ is the number of product-sum calculations of the data on the pixels of the images of the different analytic regions $A_1$ and $A_2$ of the frame $f_i$, $M_{1i}$ is the total number of data on the pixels of the image of the analytic region $A_1$ of the frame $f_i$, and $M_{2i}$ is the total number of data on the pixels of the image of the analytic region $A_2$ of the frame $f_i$.

4. Two pixels of each data pair belong to the images of different analytic regions, and belong to the image of the different frame. In this case, pairs of data on the pixels in different analytic regions in the images of different frames are used to perform a correlation calculation. This correlation calculation is a cross-correlation calculation.

$$G_{3ddc}(\xi, \psi, \eta) = \frac{\sum I_{1f_i}(x, y, z) * I_{2f_j}(x+\xi, y+\psi, z+\eta)/M_{12ij}}{(\sum I_{1f_i}(x, y, z)/M_{1i})(\sum I_{2f_j}(x, y, z)/M_{2j})} \quad (8)$$

where $G_{3ddc}$ is a cross-correlation value between the analytic region $A_1$ of the frame $f_i$ and the analytic region $A_2$ of the same $f_j$, $I_{1fi}$ is data, for example, fluorescence intensity data on the pixels of the image of the analytic region $A_1$ of the frame $f_i$, $I_{2fj}$ is data, for example, fluorescence intensity data on the pixels of the image of the analytic region $A_2$ of the frame $f_j$, x, y, z are spatial coordinates of a measurement point, $\xi$, $\psi$, $\eta$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$ is the total number of data on the pixels of the image of the analytic region $A_1$ of the frame $f_i$, and $M_{2j}$ is the total number of data on the pixels of the image of the analytic region $A_2$ of the frame $f_j$.

The data on each pixel used in the correlation calculation may be the data on this pixel, or may be the statistics of data on multiple pixels including the above pixel. The multiple pixels may be, for example, a pixel of interest and a pixel adjacent thereto. The statistics may be any one of, for example, the average value, maximum value, minimum value, relative difference, absolute difference, and relative ratio of the data on the pixels. Which statistics to use is determined by which kind of information to be obtained by the analysis according to the RICS.

The data used in the correlation calculation may be a pixel time, a line time, a frame time, a pixel position relation, a pixel size, or the statistics thereof.

Regarding the correlation calculation, each image is reconstructed on the basis of data on the pixels, and a correlation calculation may be performed for the reconstructed image. For example, the data on the adjacent pixels may be added together to reduce the number of data on the pixels to half. Alternatively, the data on one pixel is divided into multiple data. Normally, the number of data on a pixel does not increase once an image is acquired. However, on the assumption that the intensity of the acquired data on the pixel is spread around this data on the pixel by the Gaussian distribution, data on the pixel that are not normally acquired are supplemented. The number of data on the pixel does not increase in essence, but the image appears better.

(Step S6)

A fitting is performed for the result of the correlation calculation in Step 5. Thus, at least one of the number of molecules and a diffusion time is estimated. The calculation formula to be applied to the fitting varies by whether the image of the analytic region is a two-dimensional image or a three-dimensional image.

The calculation formula to be applied to the two-dimensional image is as follows.

$$G_s(\xi, \psi) = S(\xi, \psi) * G(\xi, \psi) \quad (9)$$

$$S(\xi, \psi) = \exp\left(-\frac{\frac{1}{2}*\left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{1}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is a spatial correlation value of RICS, S is the influence of a scan in an analysis of the RICS, G is the influence of a time delay in the analysis of the RICS, D is a diffusion constant, $\delta_r$ is a pixel size, N is the number of molecules, $\xi, \psi$ are variations of spatial coordinates, $W_0$ is the lateral radius of an excitation laser beam, $W_Z$ is the longitudinal radius of the excitation laser beam, $\tau_p$ is a pixel time, $\tau_l$ is a line time, and $\tau_f$ is a frame time.

The calculation formula to be applied to the three-dimensional image is as follows.

$$G_s(\xi, \psi, \eta) = S(\xi, \psi, \eta) * G(\xi, \psi, \eta) \quad (10)$$

$$S(\xi, \psi, \eta) = \exp\left(-\frac{\frac{1}{2}*\left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1 + \frac{4D(\tau_p\xi + \tau_l\psi + \tau_f\eta)}{W_0^2}\right)}\right)$$

$$G(\xi, \psi, \eta) = \frac{1}{N}$$
$$\left(\left(1 + \frac{4D(\tau_p\xi + \tau_l\psi + \tau_f\eta)}{W_0^2}\right)^{-1} * \left(1 + \frac{4D(\tau_p\xi + \tau_l\psi + \tau_f\eta)}{W_Z^2}\right)^{-1/2}\right)$$

where $G_s$ is a spatial correlation value of RICS, S is the influence of a scan in an analysis of the RICS, G is the influence of a time delay in the analysis of the RICS, D is a diffusion constant, $\delta_r$ is a pixel size, N is the number of molecules, $\xi, \psi, \eta$ are variations of spatial coordinates, $W_0$ is the lateral radius of an excitation laser beam, $W_Z$ is the longitudinal radius of the excitation laser beam, $\tau_p$ is a pixel time, $\tau_l$ is a line time, and $\tau_f$ is a frame time.

The number of molecules and the diffusion constant are found by a residual comparison (fitting) between the theoretical values in Equation (1) to Equation (8) and the results of the correlation calculations that use measured values. In the fitting, first, (a) a predetermined diffusion constant D and the number of molecules N are used to calculate $G_s$ (hereinafter, a theoretical correlation value $G_s$), which is obtained as a theoretical value. (b) The theoretical correlation value $G_s$ is then compared with a correlation value $G_s$, which is obtained as a measured value (hereinafter, a measured correlation value $G_s$), and a residual therebetween is calculated. (c) The diffusion constant D and the number of molecules N in the theoretical correlation value $G_s$ are then changed to calculate a new theoretical correlation value $G_s$. (d) The new theoretical correlation value $G_s$ is then compared with the measured correlation value $G_s$, and a residual therebetween is calculated. (e) The residual that has been obtained in (b) is then compared with the residual that has been obtained in (d) to judge whether the residual has increased. Thus, in the fitting, (b) to (e) are repeated while the diffusion constant D and the number of molecules N in the theoretical correlation value $G_s$ are changed, and a theoretical correlation value $G_s$ that provides the minimum residual between the measured correlation value $G_s$ and the theoretical correlation value $G_s$ is finally found. The diffusion constant D and the number of molecules N in the finally obtained theoretical correlation value $G_s$ are diffusion constant D and the number of molecules N in the measured correlation value $G_s$. Thus, the fitting according to Equation (9) or Equation (10) is to estimate the optimum number of molecules or diffusion constant in the two-dimensional or three-dimensional observation region while varying the diffusion constant D and the number of molecules N in the theoretical correlation value $G_s$.

There is a relation represented by Equation (11) between the diffusion constant and the diffusion time. Therefore, the diffusion time can be found from the found diffusion constant.

$$\tau = W_0^2/4D \quad (11)$$

(Step S7)

Figure 12:
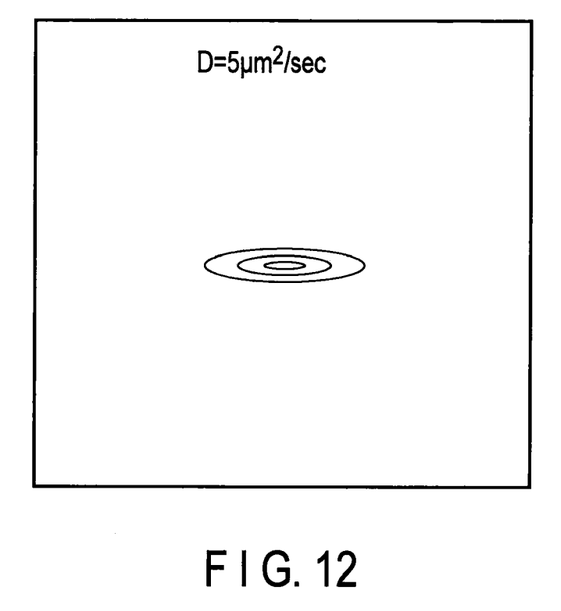
FIG. 12 is an image in which a calculation result of a spatial cross-correlation value regarding molecules in a sample is indicated by luminance.
Figure 13:
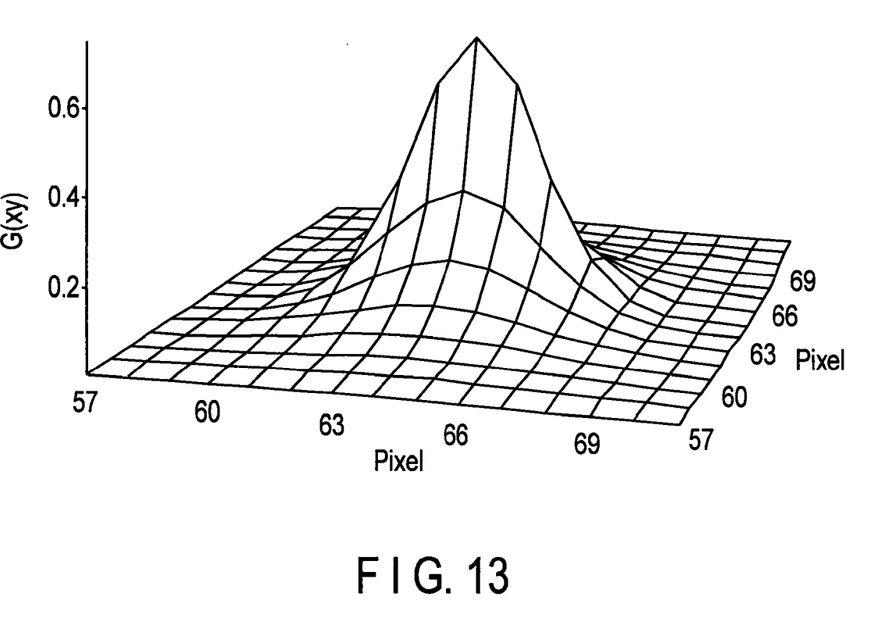
FIG. 13 shows a fitting result of the calculation result of the spatial cross-correlation value in FIG. 12.

The analytic result, for example, the image of the number of molecules or the diffusion constant is saved. If necessary, the image of the number of molecules or the diffusion constant may be displayed. The analytic result may be displayed after the end of the analyses for all the time intervals. An example of the analytic result is shown in FIG. 12 and FIG. 13. FIG. 12 shows an example of how a calculation result of a spatial correlation value regarding molecules in the sample S is displayed as an image. FIG. 13 shows a fitting result of the calculation result of the spatial correlation value in FIG. 12. In FIG. 12, the magnitude of the spatial cross-correlation value is indicated by luminance.

(Step S8)

The analysis for one time interval is finished by the operations in Step S5 to Step S7. The operations in Step S5 to Step S7 are repeated for each of the time intervals set in Step S4. That is, while the time intervals that have not been applied to the analysis still remain, the time interval applied to the analysis is changed to return to Step S5. In other words, a correlation calculation is performed for each of the time intervals, and each of the results of the correlation calculations is fitted.

The analytic result for a short time interval strongly reflects the change of a molecular species having a low molecular weight. The analytic result for a long time interval strongly reflects the change of a molecular species having a high molecular weight. That is, the correlation result for a certain time interval strongly reflects the change of a molecular species corresponding to this time interval. Therefore, the correlation analysis is performed for each of the time intervals, so that the change of each of the molecular species can be known. That is, a multicomponent analysis can be performed.

(Step S9)

If necessary, the ratio of the molecular species in the analytic region is calculated. The equation to be applied to the calculation is as follows.

$$P_{Ni} = \frac{N_i}{\sum_{k=1}^{m} N_k} \times 100\% \quad (12)$$

where $N_i$ is the number of molecules of the molecular species of an i-component, $P_{Ni}$ is the ratio of the number of molecules $N_i$ in the molecular species of the i-component, $N_k$ is the number of molecules of the molecular species of a k-component, and m is the number of components in the multicomponent analysis.

According to the present embodiment, motion, for example, can be evaluated regarding different molecules in the sample S. That is, the multicomponent analysis is possible. For example, the motions of the molecules moving at high velocities and the molecules moving at moderate velocities can be evaluated.

While the embodiments of the present invention has been described so far with reference to the drawings, the present invention is not limited to these embodiments, and various modifications and alterations may be made without departing from the spirit thereof.

For example, the analysis of the image that is contracted by detecting the fluorescence generated from the sample S, that is, the fluorescence image has been described in the embodiments. However, the image to be analyzed is not limited to the fluorescence image. Instead of the fluorescence image, the image to be analyzed may be, for example, an image constructed by detecting phosphorescence, reflected light, visible light, chemiluminescence, bioluminescence, or scattered light.

Although the image acquired by the raster scan has been described in the embodiments, the image is not limited to the image acquired by the raster scan. The image has only to be an image comprising pixels in which data on the pixels are acquired in a time-series manner. The image may be an image acquired by some other scanning method. Moreover, the image may be an image acquired by a two-dimensional image pickup device such as a CCD or a CMOS. In this case, an image of one frame comprises pixels the data of which have been simultaneously acquired, and acquiring images of multiple frames is assumed in Step S1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image analysis method comprising:
acquiring an image of at least one frame that comprises pixels;
setting at least one analytic region for the image of at least one frame;
extracting data on the pixel corresponding to each analytic region;
setting time intervals for data pairs for use in correlation calculations;
performing a correlation calculation for each of the time intervals by use of the extracted data; and
performing a fitting for each of the correlation calculation results,
wherein the acquiring the image of the at least one frame acquires images of frames, and
the setting the at least one analytic region sets analytic regions for the image of each frame, the analytic regions being the same regions in the image of each frame, respectively,
wherein the performing the correlation calculation includes performing the correlation calculation by use of pairs of data on the pixels in different analytic regions in the images of different frames.

2. The image analysis method according to claim 1, wherein the image of the analytic region is a two-dimensional image, and
the performing the correlation calculation performs the correlation calculation by use of the following equation:

$$G_{2ddc}(\xi, \psi) = \frac{\sum I_{1f_i}(x, y) * I_{2f_j}(x+\xi, y+\psi)/M_{12ij}}{(\sum I_{1f_i}(x, y)/M_{1i})(\sum I_{2f_j}(x, y)/M_{2j})}$$

where $G_{2ddc}$ is a cross-correlation value between the analytic region $A_1$ of the frame $f_i$ and the analytic region $A_2$ of the same $f_j$, $I_{1f_i}$ is data, for example, fluorescence intensity data on the pixels of the image of the analytic region $A_1$ of the frame $f_i$, $I_{2f_j}$ is data, for example, fluorescence intensity data on the pixels of the image of the analytic region $A_2$ of the frame $f_j$, x, y are spatial coordinates of a measurement point, $\xi$, $\psi$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$, is the total number of data on the pixels of the image of the analytic region $A_1$ of the frame $f_i$, and $M_{2j}$ is the total number of data on the pixels of the image of the analytic region $A_2$ of the frame $f_j$.

3. The image analysis method according to claim 1, wherein the image of the analytic region is a three-dimensional image,
the performing the correlation calculation performs the correlation calculation by use of the following equation:

$$G_{3ddc}(\xi, \psi, \eta) = \frac{\sum I_{1f_i}(x, y, z) * I_{2f_j}(x+\xi, y+\psi, z+\eta)/M_{12ij}}{(\sum I_{1f_i}(x, y, z)/M_{1i})(\sum I_{2f_j}(x, y, z)/M_{2j})}$$

where $G_{3ddc}$ is a cross-correlation value between the analytic region $A_1$ of the frame $f_i$ and the analytic region $A_2$ of the same $f_j$, $I_{1f_i}$ is data, for example, fluorescence intensity data on the pixels of the image of the analytic region $A_1$ of the frame $f_i$, $I_{2f_j}$ is data, for example, fluorescence intensity data on the pixels of the image of the analytic region $A_2$ of the frame $f_j$, x, y, z are spatial coordinates of a measurement point, $\xi$, $\psi$, $\eta$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$, is the total number of data on the pixels of the image of the analytic region $A_1$ of the frame $f_i$, and $M_{2j}$ is the total number of data on the pixels of the image of the analytic region $A_2$ of the frame $f_j$.

4. The image analysis method according to claim 3, wherein the performing the fitting performs the fitting by use of the following equation:

$$G_S(\xi, \psi, \eta) = S(\xi, \psi, \eta) * G(\xi, \psi, \eta)$$

$$S(\xi, \psi, \eta) = \exp\left(-\frac{\frac{1}{2}*\left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1+\frac{4D(\tau_p\xi+\tau_l\psi+\tau_f\eta)}{W_0^2}\right)}\right)$$

$$G(\xi, \psi, \eta) = \frac{1}{N}\left(\left(1+\frac{4D(\tau_p\xi+\tau_l\psi+\tau_f\eta)}{W_0^2}\right)^{-1} * \left(1+\frac{4D(\tau_p\xi+\tau_l\psi+\tau_f\eta)}{W_Z^2}\right)^{-1/2}\right)$$

where $G_s$ is a spatial correlation value of RIGS, S is the influence of a scan in an analysis of the RIGS, G is the influence of a time delay in the analysis of the RIGS, D is a diffusion constant, $\delta_r$ is a pixel size, N is the number of molecules, $\xi$, $\psi$, $\eta$ are variations of spatial coordinates, $W_0$ is the lateral radius of an excitation laser beam, $W_Z$ is the longitudinal radius of the excitation laser beam, $\tau_p$ is a pixel time, $\tau_l$ is a line time, and $\tau_f$ is a frame time.

5. The image analysis method according to claim 1, further comprising estimating the number of molecules of a molecular species of each component in the analytic region by performing the fitting, and calculating the ratio of the molecular species by use of the following equation:

$$P_{Ni} = \frac{N_i}{\sum_{k=1}^{m} N_k} \times 100\%$$

where $N_i$ is the number of molecules of the molecular species of an i-component, $P_{Ni}$ is the ratio of the number of molecules $N_i$ in the molecular species of the i-component, $N_k$ is the number of molecules of the molecular species of a k-component, and m is the number of components in the multicomponent analysis.

6. The image analysis method according to claim 1, further comprising reconstructing data on the pixels in the analytic region, wherein the performing the correlation calculation performs the correlation calculation by use of the reconstructed data.

7. The image analysis method according to claim 1, wherein the image of each frame comprises pixels the data of which are acquired in a time-series manner by light scanning.

8. The image analysis method according to claim 1, further comprising displaying a correlation calculation result.

9. An image analysis apparatus comprising:
an image acquiring section to acquire an image of at least one frame that comprises pixels;
an analytic region setting section to set at least one analytic region for the image of at least one frame;
a data extracting section to extract data on the pixel corresponding to each analytic region;
a time interval setting section to set time intervals for data pairs for use in correlation calculations; and
an analytic processing section to perform a correlation calculation for each of the time intervals by use of the extracted data, and a fitting for each of the correlation calculation results,
wherein the image acquiring section acquires images of frames, and
the analytic region setting section sets analytic regions for the image of each frame, the analytic regions being the same regions in the image of each frame, respectively,
wherein the analytic processing section performs the correlation calculation by use of pairs of data on the pixels in different analytic regions in the images of different frames.

10. The image analysis apparatus according to claim 9, wherein the image of the analytic region is a two-dimensional image, and
the analytic processing section performs the correlation calculation by use of the following equation:

$$G_{2ddc}(\xi, \psi) = \frac{\sum I_{1f_i}(x, y) * I_{2f_j}(x + \xi, y + \psi)/M_{12ij}}{(\sum I_{1f_i}(x, y)/M_{1i})(\sum I_{2f_j}(x, y)/M_{2j})}$$

where $G_{2ddc}$ is a cross-correlation value between the analytic region $A_1$ of the frame $f_i$ and the analytic region $A_2$ of the same $f_j$, $I_{1fi}$ is data, for example, fluorescence intensity data on the pixels of the image of the analytic region $A_1$ of the frame $f_i$, $I_{2fj}$ is data, for example, fluorescence intensity data on the pixels of the image of the analytic region $A_2$ of the frame $f_j$, x, y are spatial coordinates of a measurement point, $\xi$, $\psi$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$ is the total number of data on the pixels of the image of the analytic region $A_1$ of the frame $f_i$, and $M_{2j}$ is the total number of data on the pixels of the image of the analytic region $A_2$ of the frame $f_j$.

11. The image analysis apparatus according to claim 9, wherein the image of the analytic region is a three-dimensional image,
the analytic processing section performs the correlation calculation by use of the following equation:

$$G_{3ddc}(\xi, \psi, \eta) = \frac{\sum I_{1f_i}(x, y, z) * I_{2f_j}(x + \xi, y + \psi, z + \eta)/M_{12ij}}{(\sum I_{1f_i}(x, y, z)/M_{1i})(\sum I_{2f_j}(x, y, z)/M_{2j})}$$

where $G_{3ddc}$ is a cross-correlation value between the analytic region $A_1$ of the frame $f_i$ and the analytic region $A_2$ of the same $f_j$, $I_{1fi}$ is data, for example, fluorescence intensity data on the pixels of the image of the analytic region $A_1$ of the frame $f_i$, $I_{2fj}$ is data, for example, fluorescence intensity data on the pixels of the image of the analytic region $A_2$ of the frame $f_j$, x, y, z are spatial coordinates of a measurement point, $\xi$, $\psi$, $\eta$ are variations of the spatial coordinates from the measurement point, $M_{12ij}$ is the number of product-sum calculations of the data on the pixels of the images of the analytic region $A_1$ of the frame $f_i$ and the analytic region $A_2$ of the frame $f_j$, $M_{1i}$ is the total number of data on the pixels of the image of the analytic region $A_1$ of the frame $f_i$, and $M_{2j}$ is the total number of data on the pixels of the image of the analytic region $A_2$ of the frame $f_j$.

12. The image analysis apparatus according to claim 11, wherein the analytic processing section performs the fitting by use of the following equation:

$$G_S(\xi, \psi, \eta) = S(\xi, \psi, \eta) * G(\xi, \psi, \eta)$$

$$S(\xi, \psi, \eta) = \exp\left(-\frac{\frac{1}{2} * \left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1 + \frac{4D(\tau_p\xi + \tau_l\psi + \tau_f\eta)}{W_0^2}\right)}\right)$$

$$G(\xi, \psi, \eta) = \frac{1}{N}\left(\left(1 + \frac{4D(\tau_p\xi + \tau_l\psi + \tau_f\eta)}{W_0^2}\right)^{-1} * \left(1 + \frac{4D(\tau_p\xi + \tau_l\psi + \tau_f\eta)}{W_Z^2}\right)^{-1/2}\right)$$

where $G_s$ is a spatial correlation value of RIGS, S is the influence of a scan in an analysis of the RIGS, G is the influence of a time delay in the analysis of the RIGS, D is a diffusion constant, $\delta_r$ is a pixel size, N is the number of molecules, $\xi$, $\psi$, $\eta$ are variations of spatial coordinates, $W_0$ is the lateral radius of an excitation laser beam, $W_Z$ is the longitudinal radius of the excitation laser beam, $\tau_p$ is a pixel time, $\tau_l$ is a line time, and $\tau_f$ is a frame time.

13. The image analysis apparatus according to claim 9, the analytic processing section estimates the number of molecules of a molecular species of each component in the analytic region by performing the fitting, and calculates the ratio of the molecular species by use of the following equation:

$$P_{Ni} = \frac{N_i}{\sum_{k=1}^{m} N_k} \times 100\%$$

where $N_i$ is the number of molecules of the molecular species of an i-component, $P_{Ni}$ is the ratio of the number of molecules $N_i$ in the molecular species of the i-component, $N_k$ is the number of molecules of the molecular species of a k-component, and m is the number of components in the multicomponent analysis.

14. The image analysis apparatus according to claim 9, the analytic processing section reconstructs data on the pixels in the analytic region, and performs the correlation calculation by use of the reconstructed data.

15. The image analysis apparatus according to claim 9, wherein the image of each frame comprises pixels the data of which are acquired in a time-series manner by light scanning.

16. The image analysis apparatus according to claim 9, further comprising a displaying section to display a correlation calculation result.

* * * * *